US011712197B2

(12) United States Patent
Varghese et al.

(10) Patent No.: US 11,712,197 B2
(45) Date of Patent: Aug. 1, 2023

(54) OPTICAL SKIN SENSOR USING OPTIMAL SPECTRAL BANDS TO MINIMIZE THE EFFECT OF PROBE PRESSURE

(71) Applicant: KONINKLIJKE PHILIPS N.V., Eindhoven (NL)

(72) Inventors: Babu Varghese, Eindhoven (NL); Cornelis Willem Hameetman, Rotterdam (NL); Walter Hermans, Overpelt (BE); Arnold Johannes Martinus Jozeph Ras, Mierlo (NL)

(73) Assignee: KONINKLIIKE PHILIPS N.V., Eindhoven (NL)

( * ) Notice: Subject to any disclaimer, the term of this patent is extended or adjusted under 35 U.S.C. 154(b) by 262 days.

(21) Appl. No.: 16/957,138

(22) PCT Filed: Dec. 27, 2018

(86) PCT No.: PCT/EP2018/086892
§ 371 (c)(1),
(2) Date: Jun. 23, 2020

(87) PCT Pub. No.: WO2019/129796
PCT Pub. Date: Jul. 4, 2019

(65) Prior Publication Data
US 2020/0330027 A1     Oct. 22, 2020

(30) Foreign Application Priority Data

Dec. 28, 2017  (EP) .................................... 17210781

(51) Int. Cl.
*A61B 5/00*      (2006.01)
(52) U.S. Cl.
CPC ............ *A61B 5/443* (2013.01); *A61B 5/0077* (2013.01); *A61B 5/448* (2013.01); *A61B 2562/0233* (2013.01)

(58) Field of Classification Search
CPC ....... A61B 5/443; A61B 5/0077; A61B 5/448; A61B 2562/0233; A61B 2560/0406;
(Continued)

(56) References Cited

U.S. PATENT DOCUMENTS 6,070,092 A   5/2000  Kazama
6,993,167 B1  1/2006  Skladnev
(Continued)

FOREIGN PATENT DOCUMENTS

KR         101142438 B1    5/2012

OTHER PUBLICATIONS

International Search Report and Written Opinion dated Mar. 21, 2019 for International Application No. PCT/EP2018/086892 Filed Dec. 27, 2018.
(Continued)

*Primary Examiner* — David J Bolduc

(57) ABSTRACT

The invention provides a system (1) comprising a sensor (100) for measuring a skin parameter, the sensor (100) comprising a plurality of spatially separated light sources (110) configured to provide light source light (111), and one or more detectors (120) configured at a first distance (d1) from each of the light sources (110), wherein the first distance (d1) is selected from the range of 5-80 mm, wherein the sensor (100) is configured to provide the light source light (111) with optical axes (OL) under an angle (a) relative to an optical axis (O2) of the one or more detectors (120) selected from the range of 10-80°, wherein the sensor (100) comprises at least three light sources (110), wherein the light sources (110) are configured to provide unpolarized light source light (111), wherein the system (1) further comprises an analysis system (2) wherein the analysis system (2) is configured to generate a corresponding skin sensor value on the basis of a detector response of the one or more detectors
(Continued)

(120) at one or more wavelengths selected from a spectral range of 350-780 nm.

20 Claims, 5 Drawing Sheets

(58) Field of Classification Search
CPC ... A61B 5/444; A61B 5/14558; A61B 5/6843; A61B 2562/043
See application file for complete search history.

(56) References Cited

U.S. PATENT DOCUMENTS

| | | | |
|---|---|---|---|
| 7,289,211 B1* | 10/2007 | Walsh, Jr. | G01J 4/04 356/369 |
| 2003/0045799 A1* | 3/2003 | Bazin | G01N 21/84 600/476 |
| 2004/0201846 A1* | 10/2004 | Mullani | G01N 21/6447 356/369 |
| 2009/0318908 A1* | 12/2009 | Van Pieterson | A61N 5/062 606/9 |
| 2010/0253225 A1* | 10/2010 | Lifka | A61N 5/0616 438/42 |
| 2011/0304705 A1* | 12/2011 | Kantor | G06T 7/586 348/E13.074 |
| 2012/0062364 A1 | 3/2012 | Rowe | |
| 2013/0085351 A1* | 4/2013 | Kudavelly | A61B 5/14558 600/315 |
| 2014/0243685 A1* | 8/2014 | Patwardhan | A61B 5/44 600/476 |
| 2015/0062380 A1* | 3/2015 | Nakamura | A61B 5/0077 348/234 |
| 2015/0164327 A1* | 6/2015 | Yaroslavsky | G01N 21/21 600/407 |
| 2015/0223749 A1* | 8/2015 | Park | G01N 21/6486 600/476 |
| 2017/0224270 A1 | 8/2017 | Stamnes | |
| 2018/0184894 A1* | 7/2018 | Su | A61B 3/102 |
| 2018/0279942 A1* | 10/2018 | Houjou | A61B 5/0077 |
| 2018/0360373 A1* | 12/2018 | Aarts | A61B 5/14507 |
| 2020/0337603 A1* | 10/2020 | Hazen | A61B 5/0051 |

OTHER PUBLICATIONS

Atencio, et al: "Influence of Probe Pressure on Human Skin Diffuse Reflectance Spectroscopy Measurements", Optical Memory and Neural Networks (Information Optics), 2009, vol. 18, No. 1, pp. 6-14.
Bender, et al: "Noninvasive monitoring of tissue hemoglobin using UV-VIS diffuse reflectance spectroscopy: a pilot study", Dec. 21, 2009 / vol. 17, No. 26 / Optics Express.
Reif, et al: "Analysis of changes in reflectance measurements on biological tissues subjected to different probe pressures", Journal of Biomedical Optics, Jan./Feb. 2008, vol. 13(1).

* cited by examiner

OPTICAL SKIN SENSOR USING OPTIMAL SPECTRAL BANDS TO MINIMIZE THE EFFECT OF PROBE PRESSURE

CROSS REFERENCE TO RELATED APPLICATIONS

This application is the U.S. National Phase application under 35 U.S.C. § 371 of International Application No. PCT/EP2018/086892 filed Dec. 27, 2018, published as WO 2019/129796 on Jul. 4, 2019, which claims the benefit of European Patent Application Number 17210781.5 filed Dec. 28, 2017. These applications are hereby incorporated by reference herein.

FIELD OF THE INVENTION

The invention relates to a system comprising a sensor for measuring a skin parameter, such as skin gloss and/or skin oiliness. The invention further relates to a method for evaluation of a skin parameter, such as skin gloss and/or skin oiliness.

BACKGROUND OF THE INVENTION

The appearance of skin is significantly influenced by the presence of a thin emulsified film on the skin surface. Sebum containing lipids from sebaceous glands and epidermal keratinocytes is mixed with sweat and other lipids from cosmetics and environment to form this emulsified film of refractive index higher than that of epidermis. Sebum causes the skin to look glossier due to higher Fresnel reflection and smooth air-sebum interface. Optimal balance between sebum production and requirements imparts a non-glossy and healthy feel to the skin and is dermatologically and cosmetically desirable. Glossy and oily skin is considered to be unaesthetic and unpleasant and often associated with various dermatological disorders such as seborrhea, acne and hormonal imbalance. In sebum deficit conditions, the skin is vulnerable to infections and it feels itchy, dry, and looks lusterless, erythematous, and scaly.

As a result strategies to balance the needs of the skin to its optimal lipid requirements by controlling the sebum secretion rate and/or to monitor the skin condition using non-invasive optical devices and methods seem necessary.

Devices for measuring skin glossiness (or "skin glossiness") are known in the art. However, for (reliable) home use, such devices are not available. Skin gloss and oiliness measurements using the camera prototype resulting from specular reflections depends on the physical properties of the skin, such as refractive index, texture and device characteristics, such as device geometry, angle of incidence and polarization of the incident radiation. For a given optical geometry, skin gloss and oiliness measurements are significantly influenced by the pressure applied on the skin. Hence, it appears that a measurement of e.g. skin gloss and oiliness characteristics using an optical sensor may (also) depend on the applied pressure (of the device) on to the skin. This could result in non-quantitative estimation of skin gloss and oiliness value and thus deteriorate the quality of the information that can be potentially offered to the consumers. This effect of applied pressure on skin gloss and oiliness measurements are influenced by doming of skin and also changes in the reflectance spectra due to the changes in the amount of blood in the measurement volume. Hence, present devices may suffer from undesired artefacts.

Analysis of the skin is known in the art. U.S. Pat. No. 6,993,167, for instance, describes a system for collecting, storing and displaying dermatological images for the purpose of monitoring and diagnosis of skin conditions and skin cancers, including melanoma. A hand-held unit illuminates a section of the patient's skin, and an imaging device generates imaging signals from light derived from a skin section. Pairs of light output ports in the hand-held unit are arranged such that their intensity distributions overlap at their half-intensity levels so that the resulting summation of their intensities has a flat central region. Three image stores are maintained, one for lesion images, one for "nearby skin" images, and one for reference-white images. The "nearby skin" images are used by the system software to automatically determine the skin/lesion border. The reference white images are used to set the dynamic range of the instrument and to compensate for lighting irregularities. Two images of the same lesion taken at different times may be displayed simultaneously so that changes in the lesion may be determined. The calibration system is designed so that image data taken on any of multiple machines built to the same specification will be corrected back to a common reference standard to ensure absolute accuracy in color rendition.

US2012062364 describes a biometric system with an optically adaptive interface. In some embodiments, an optically adaptive interface changes optical characteristics in response to the placement of a finger on the optically adaptive interface. In some embodiments, the optically adaptive interface can include an active layer and a surface layer. The active layer and the surface layer can have different optical properties. For example, one layer may be opaque and the other transparent, the two layers may have complementary colors, the two layers may have orthogonal polarization reflectors, one layer may be reflective and the other absorptive, etc. Moreover, the active layer can be a fluid with either high or low viscosity. For example, the viscosity can be such that the active layer fluid is either completely displaced or not displaced in locations corresponding to finger valleys.

SUMMARY OF THE INVENTION

It is an aspect of the invention to provide an alternative device (herein further the more general term "system" is applied) and/or skin (gloss) sensing method, which preferably further at least partly obviate(s) one or more of above-described drawbacks. The present invention may have as object to overcome or ameliorate at least one of the disadvantages of the prior art, or to provide a useful alternative.

Amongst others, the invention proposes a ((low-cost) camera) system for (quantitative) measurement of e.g. skin gloss and oiliness that is less dependent on the applied pressure. Especially, by using specific spectral bands (such as especially one or more of 370-740 nm, 360-420 nm, 600-650 nm) the effect of pressure on the measured skin may be minimized. In the case of white light illumination, the optimal spectral bands may be about 370-740 nm, 370-420 nm, and 600-650 nm. Other spectral bands, such as 440-500 nm, 520-620 nm and 640-740 nm showed high sensitivity to the probe pressure through changes in reflectance spectrum and therefore are not preferred for quantifying skin gloss and oiliness.

Hence, in an aspect the invention provides a system comprising a sensor for measuring a skin parameter, the sensor comprising a plurality of spatially separated light sources configured to provide light source light, and one or more detectors configured at a first distance (d1) from each of the light sources, wherein the first distance (d1) is selected from the range of 5-80 mm, wherein the sensor is configured to provide the light source light with optical axes (OL) under an angle (α) relative to an optical axis (O2) of the sensor selected from the range of 10-80°, wherein the sensor comprises one or more light sources, especially at least three light sources, wherein the light sources are especially configured to provide unpolarized light source light, wherein the system further comprises an analysis system wherein the analysis system is configured to generate a corresponding skin sensor value on the basis of a detector response of the one or more detectors at one or more wavelengths selected from a spectral range of 350-780 nm.

The use of such system may allow a reduction of the impact of different pressures on the skin on the skin parameter to be evaluated. Even though the user may apply different pressures, or different users may apply different pressures, the skin parameter, especially the skin oiliness, may be evaluated with the present system at least partly, or even essentially, independent of such pressure. This improves the reliability of the system.

Especially, the system may be used to measure a skin parameter. Hence, the system may especially be configured to measure a skin parameter. Alternatively or additionally, the system may also be used to measure a hair parameter. Hence, the system may alternatively or additionally (also) be configured to measure a hair parameter. Alternatively or additionally, the system may also be used to measure a parameter of another part of the body, such for measuring a part of the eye ball or an oral cavity. Hence, the system may alternatively or additionally (also) be configured to measure a parameter of a part of the body not being the skin or hair.

Especially, the skin parameter is selected from the group consisting of skin gloss, skin oiliness, and skin hydration, such as especially skin oiliness. Further, with such system it may be possible to quantitatively estimate skin gloss. The term "skin gloss" herein refers to gloss of the skin but may also refer to "skin oiliness". Hence, the term "skin gloss" herein may also be defined as "skin parameter especially selected from one or more of the group consisting of skin gloss and skin oiliness". The values that may be measured with the system as described herein may reflect skin gloss and skin oiliness, as skin gloss may be related to skin oiliness. Herein, the term "skin gloss" is sometimes used to indicate both skin gloss or skin oiliness. Hence, in embodiments the term skin gloss may refer to skin gloss or skin oiliness, or especially to skin gloss.

As indicated above, the invention provides a system comprising a sensor. The term "system" may refer to a single device, e.g. having its own housing, but may also refer to a plurality of functionally coupled devices, such as e.g. the sensor and a control system or a control system comprising device, such as a computer, a smartphone etc. In embodiments, the term "sensor" may also refer to a plurality of sensors. For instance, a device may comprise the sensor, and another device may comprise the analysis system; such devices may functionally be coupled to provide the system.

The system may include a memory, a processing device (or "processor" or "processor system" or "controller" or "control system"), a user interface, and an indication unit for indicating a sensed skin gloss value, such as a LED indicator (e.g. suitable for indicating different values by switching on 0-n LEDs in dependence of the sensed value, wherein n is the number of LEDs used for indicating a maximum sensed value, with n in general being equal to or larger than two, such as at least three) and/or a display.

Examples of user interface devices include a manually actuated button, a display, a touch screen, a keypad, a voice activated input device, an audio output, an indicator (e.g., lights), a switch, a knob, a modem, and a networking card, among others. Especially, the user interface device may be configured to allow a user instruct the device or apparatus with which the user interface is functionally coupled by with the user interface is functionally comprised. The user interface may especially include a manually actuated button, a touch screen, a keypad, a voice activated input device, a switch, a knob, etc., and/or optionally a modem, and a networking card, etc. The user interface may comprise a graphical user interface. The term "user interface" may also refer to a remote user interface, such as a remote control. A remote control may be a separate dedicate device. However, a remote control may also be a device with an App configured to (at least) control the system or device or apparatus.

The controller/processor and the memory may be any type. The processor may be capable of performing the various described operations and executing instructions stored in the memory. The processor may be an application-specific or general-use integrated circuit(s). Further, the processor may be a dedicated processor for performing in accordance with the present system or may be a general-purpose processor wherein only one of many functions operates for performing in accordance with the present system. The processor may operate utilizing a program portion, multiple program segments, or may be a hardware device utilizing a dedicated or multi-purpose integrated circuit.

The sensor comprises a plurality of spatially separated light sources configured to provide light source light ("light"). Especially, the sensor comprises at least three spatially separated light sources.

The term "light source" may comprise a semiconductor light-emitting device, such as a light emitting diode (LEDs), a resonant cavity light emitting diode (RCLED), a vertical cavity laser diode (VCSELs), an edge emitting laser, etc. The term "light source" may also refer to an organic light-emitting diode, such as a passive-matrix (PMOLED) or an active-matrix (AMOLED). In a specific embodiment, the light source comprises a solid state light source (such as a LED or laser diode). In an embodiment, the light source comprises a LED (light emitting diode). The term LED may also refer to a plurality of LEDs. Further, the term "light source" may in embodiments also refer to a so-called chips-on-board (COB) light source. The term "COB" especially refers to LED chips in the form of a semiconductor chip that is neither encased nor connected but directly mounted onto a substrate, such as a PCB. Hence, a plurality of semiconductor light sources may be configured on the same substrate. In embodiments, a COB is a multi LED chip configured together as a single lighting module.

Further, the light sources are configured to provide unpolarized light source light. This allows the sensor derive information from the polarization direction of the reflected light.

The light sources may be configured to provide one or more of UV, visible light and infrared light (especially near infrared light). The visible light may be white light. The IR light may e.g. especially be radiation having a wavelength selected from the range of 750-3000 nm. Especially, however, the light sources are at least configured to provide light in UV and visible, or at least the visible. Visible light has a wavelength selected from the range of 380-780 nm.

In embodiments, the light sources are especially configured to provide white light. The term white light herein, is known to the person skilled in the art. It may especially relate to light having a correlated color temperature (CCT) between about 2000 and 20000 K, especially 2700-20000 K, for general lighting especially in the range of about 2700 K and 6500 K, and for backlighting purposes especially in the range of about 7000 K and 20000 K, and especially within about 15 SDCM (standard deviation of color matching) from the BBL (black body locus), especially within about 10 SDCM from the BBL, even more especially within about 5 SDCM from the BBL. Especially, the white light may be provided by a blue LED with a yellow emitting luminescent material. Such light source can provide white light that is essentially not polarized.

Alternatively, the light sources may be configured to generate colored light; this will be further explained below. Yet, in further embodiments the system may comprise a mode wherein white light is applied and a mode wherein colored light is applied, or a mode wherein alternatingly white light and colored light is applied.

Especially, the sensor comprises a plurality of spatially separated light sources. This implies that there is some distance between the light sources. Especially, the light sources are configured with the detector in between. Further, especially the maximum number of light sources is about twelve, such as ten, like eight, such as six or four or three. Up to about twelve, even more especially up to about eight, such as up to about six allows a configuration around the sensor which also allows a spatial separation between adjacent light sources which may (also) be in the order of about 1-100 mm, such as at least 5 mm, like at least 10 mm. Especially, the system is configured to sequentially provide the light source light of the different light sources. Hence, the light sources may sequentially be driven, which may allow deriving additional information from the reflection of the light.

Hence, in embodiments the system comprises at least three light sources. In yet further embodiments, the sensor has a sensor optical axis, and the light sources are configured rotationally symmetric around the sensor optical axis. In embodiments, the light sources may be configured relative to each other under angles with the optical axis of 360°/n, wherein n is the number of light sources. Hence, in embodiments wherein the system comprises at least three or four light sources, the mutual angles with the optical axis may be 120° and 90°, respectively.

Therefore, as indicated above, the system comprises especially at least two light sources, even more especially at least three light sources, and the light sources are especially configured to provide unpolarized (visible) light source light, even more especially white light.

As further indicated above, the system also comprises a detector configured at a first distance (d1) from each of the light sources. Good results were obtained with the first distance (d1) being in the range of about 1-80 mm. Hence, in specific embodiment the first distance may by be selected from the range of 1-80 mm, especially from the range of 2-60 mm, such as in the range of 5-80 mm, like especially 4-20 mm, such as 5-20 mm, like in the range of 6-14 mm. Hence, in embodiments the first distance (d1) may be selected from the range of about 4-20 mm, such as 6-14 mm, like especially about 8-14 mm.

Especially, the detector is configured to detect polarized light. To this end, the detector may comprise a polarizer, which is configured downstream of the detector. In this way, only polarized light, especially S-polarized light, may be received by the detector. Below, some specific embodiments of the polarizer are further elucidated.

In specific embodiments, the sensor is configured to provide the light source light with optical axes (OL) under an angle of incidence ($\alpha$), especially selected from the range of 10-80°, with the skin at a third distance (d3) and to detect reflected light source light (reflected at the skin). Of course, the skin is not part of the system. However, the system is especially configured to measure skin at a third distance. For instance, the system may include a distance holder or other element, which allows configuration of the sensor at the third distance. At this distance, the above indicated angle of incidence may be achieved, which is in the range of 10-80°, more especially 20-80°. In specific embodiments, which are further elucidated below, the angle is selected from the range of 20-60°.

Therefore, in specific embodiments the sensor is configured to provide the light source light with optical axes under an angle (a) relative to an optical axis (O2) of the sensor selected from the range of 10-80°. Further, in embodiments the angle (a) may especially be selected from the range of 20-60°.

Hence, in embodiments the sensor may especially be configured to detect reflected light source light, with the skin at a third distance (d3).

In specific embodiments, the detector comprises a 2D camera, such as a CCD camera TD-Next 5620 M7_1A and TD-Next 5640 M12_3B. Each pixel may essentially consist of three pixels for blue, green, and red, respectively. This may provide the detector blue, green, and red channels intensity separately.

In embodiments, the detector may have a detector area of about 10*10 mm$^2$. The detector may have in the order of 1 Megapixel or more.

In further embodiments, the sensor may further comprise a focusing lens configured downstream of the detector. The focusing lens may be configured to have at one side the detector in focus and/or at the other side of the lens the skin in focus. The lens may allow a good image of the skin at the detector.

In embodiments, the sensor may further comprise an aperture configured downstream of the detector and upstream of the focusing lens. This may further add to resolution. The aperture may in embodiments have a diameter selected from the range of 0.1-5 mm, more especially 0.1-2 mm, like especially 0.1-0.8 mm.

The optical axis of the system (i.e. especially of the sensor) may be configured perpendicular to the detector as in general the detector will be configured in a central position with the light sources surrounding the detector. The optical axis of the sensor may thus essentially coincide with the optical axis of the sensor. When more than one optical detector is available, the optical axes of the optical detectors may essentially be parallel, and parallel to the optical axis of the sensor. As the detectors may be symmetrically arranged, the optical axis of the detectors may have the same distances to the optical axis of the sensor. Other configurations of the detectors may be used as well. In general, the optical axis will be perpendicular to the opening and intercept in the middle with a virtual plane parallel to the opening.

The system may further comprise an analysis system. The analysis system is configured to generate a corresponding skin sensor value in dependence of a sensor signal of the sensor. The analysis system and sensor may be incorporated in a single device, such as skin cleansing device, skin rejuvenation device, etc. Hence, in embodiments the system comprises a skin care device, like such skin cleansing device, skin rejuvenation device, etc., wherein the skin care device comprises the sensor and the analysis system. The analysis system can translate the signal of the sensor, more especially of the detector, into a signal that may contain useful information of the user, such as an indication of the skin glossiness on an indicator unit (such as a display or LED bar). The skin sensor value can be the skin parameter of may be further processed into the skin parameter based on predefined relations between the skin sensor value and the skin parameter.

In other embodiments, however, the sensor may be comprised by a separate device, that is wired or wireless coupled to an analysis system. For instance, such analysis system may be comprised by a smartphone. For instance, an App may be used to readout the sensor and display a skin sensor value based on the sensor signal generated by the sensor. Therefore, in yet other embodiments the system comprises a skin care device, wherein the skin care device comprises the sensor, and a second device functionally coupled to the skin care device, wherein the second device comprises the analysis system. The term "analysis system" may also refer to a plurality of interrelated systems. For instance, the sensor may (further) comprise a processor and an external device may comprise a processor which may communicate with each other. The processor of the sensor may provide the sensor signal, and the processor of the external device generates on the basis thereon the skin sensor value, indicative of the glossiness/oiliness of the skin.

The sensor signal may be the detector signal. In other embodiments, the sensor signal may be a processed detector signal. Hence, the phrase "base on the detector signal" may in embodiments also refer to a processed detector signal. Based on the sensor signal, i.e. essentially based on the detector signal, the analysis system may provide a corresponding skin sensor value.

When the system comprises a functional device, such as a skin cleansing device or skin rejuvenation device, the device may be configured to execute an action in dependence of the sensor signal of the sensor (for sensing gloss) (or skin sensor value). For instance, when a certain lower or upper threshold of skin gloss (or skin oiliness) is reached, the functional device may provide a signal to the user, like a sound or vibration signal. Alternatively or additionally, the functional device may reduce or increase specific actions in dependence of the sensor signal, such as in increased or reduced massaging of the skin in dependence of the sensor signal.

As indicated above, the analysis system may especially be configured to generate a corresponding skin sensor value on the basis of a detector response of the one or more detectors at one or more wavelengths selected from a spectral range of 350-780 nm. Hence, on the basis of the response of the detectors at one or more wavelengths, the skin parameter(s) can be determined. In general a plurality of wavelengths may be used, such as a (narrow) spectral band or a plurality of (narrow) spectral bands, such as a combination of spectral bands.

It appears that specific bands may especially be useful, as they are rather insensitive to pressure of the sensor on the skin. In specific embodiments, the analysis system is configured to generate a corresponding skin sensor value on the basis of one or more of a detector response of the one or more detectors in the entire wavelength range of 370-740 nm, even more especially 350-780 nm, a detector response of the one or more detectors at one or more wavelengths selected from a spectral range of 350-440 nm, and a detector response of the one or more detectors at one or more wavelengths selected from a spectral range of 580-670 nm.

Hence, the detection may be a detection wherein essentially all intensity in the wavelength range of 370-740 nm may be used as input for the skin parameter. It appears when such broad wavelength range is used, wavelength ranges with different intensity behavior as function of the pressure, essentially level each other out.

Alternatively or additionally, one or more relative narrow bands (or specific wavelengths within such spectral range) may be selected. For instance, one or more wavelengths in the spectral range of 350-440 nm, especially one or more wavelengths in the spectral range of 370-420 nm may be selected, as these are relatively insensitive to pressure. Yet, alternatively or additionally, one or more wavelengths in the spectral range of 580-670 nm, especially one or more wavelengths in the spectral range of 600-650 nm, may be selected, as also these are also relatively insensitive to pressure. Hence, in embodiments the analysis system may be configured to generate a corresponding skin sensor value on the basis of one or more of a detector response of the one or more detectors in the entire wavelength range of 370-740 nm, a detector response of the one or more detectors at one or more wavelengths selected from the spectral range of 370-420 nm, and a detector response of the one or more detectors at one or more wavelengths selected from the spectral range of 600-650 nm.

Hence, e.g. white light may be used, but also colored light may be used, or a mixture of white and colored light. The light sources may be configured to provide essentially all wavelengths in one or more of the wavelength ranges, such intensity at essentially all wavelengths selected from the range of 370-740 nm. However, in other embodiments one or more light sources may be configured to provide essentially only (e.g. at least 80% of the power) intensity at one or more wavelength in one of the narrow wavelength ranges. Hence, the spectral analysis may enabled by selecting the desired wavelength ranges for detection and/or by selecting light sources that are configured to provide the desired wavelength(s) in one or more of the (narrow) wavelength ranges. Hence, in embodiments the light sources may be configured to provide light source light only at one or more wavelengths selected from the spectral range of 370-420 nm, and/or at one or more wavelengths selected from the spectral range of 600-650 nm.

Therefore, in embodiments the analysis system may especially be configured to generate a corresponding skin sensor value on the basis of a detector response of the one or more detectors at one or more wavelengths selected from the spectral range of 370-420 nm, and a detector response of the one or more detectors at one or more wavelengths selected from the spectral range of 600-650 nm.

If desired, the narrow bands may be chosen a bit broader. Therefore, in specific embodiments the analysis system is configured to generate a corresponding skin sensor value on the basis of a detector response of the one or more detectors at one or more wavelengths selected from the spectral range of 350-440 nm, and a detector response of the one or more detectors at one or more wavelengths selected from the spectral range of 580-670 nm.

Especially reliable results may be obtained when a combination if signals in different wavelength ranges is used, such as in two or more of the herein indicated three wavelength ranges. As indicated above, this may in embodiments include two narrow ranges. However, this may in embodiments also include the combination of a narrow range with the broad range. Especially, the combination of the signal of the broad range as well as the signal in the two specific narrow wavelength ranges, may be used to determine the skin parameter(s) in a reliable way. Therefore, in embodiments the analysis system is configured to generate a corresponding skin sensor value on the basis of the detector response of the one or more detectors in the entire wavelength range of 370-740 nm, such as in specific embodiments 350-780 nm, the detector response of the one or more detectors at one or more wavelengths selected from the spectral range of 370-420 nm, such as in specific embodiments 350-440 nm, and the detector response of the one or more detectors at one or more wavelengths selected from the spectral range of 600-650 nm, such as in specific embodiments 580-670 nm. Hence, in embodiments the analysis system is configured to generate a corresponding skin sensor value on the basis of the detector response of the one or more detectors in the entire wavelength range of 370-740 nm, the detector response of the one or more detectors at one or more wavelengths selected from the spectral range of 370-420 nm (especially the entire wavelength range (of 370-420 nm)), and the detector response of the one or more detectors at one or more wavelengths selected from the spectral range of 600-650 nm (especially the entire wavelength range (of 600-650 nm)).

Alternatively, the analysis system may be configured to generate a corresponding skin sensor value on the basis of a detector response of the one or more detectors in the entire wavelength range of 370-740 nm, such as even in the entire wavelength range of 350-780 nm, (but) excluding the wavelength ranges 440-620 nm and 640-740 nm (or where applicable 640-780 nm). Hence, in specific embodiments the analysis system is configured to generate a corresponding skin sensor value on the basis of a detector response of the one or more detectors in the entire wavelength range of 350-780 nm excluding the wavelength ranges 440-620 nm and 640-780 nm.

The analysis system may analyze specific wavelength regions by ignoring other wavelength region. As indicated above, by using specific light sources, it may also be possible to provide only signal in specific wavelength regions; this may be less applicable when using the entire wavelength range of e.g. 370-740 nm.

When specific wavelength regions are (only) of interest, it may also be possible to use an optical filter. Hence, in specific embodiments, one or more detectors are configured for detection of a part of the wavelength range of 370-740 nm, such as e.g. even 350-780 nm. In such embodiments, a detector may be used that is designed for the specific wavelength range, and/or one or more optical filters may be used essentially only allowing transmission of the light in the desired part of the wavelength range, e.g. 600-650 nm.

Further, dependent upon the skin color the system may choose one or more wavelengths that may be especially relatively insensitive to pressure for the specific skin color. The term "skin color" may refer to a basic skin color, like a dark skin or a light skin, but may also refer to an average skin color, such as taking into account spots lacking in pigment or spots with an increased pigment content (like freckles). The system described herein may especially be suitable for lighter skin types, such as e.g. skin types I-IV, especially I-III, such as I-II, according to the Fitzpatrick scale. Hence, in specific embodiments the analysis system is configured to determine the type of skin for measuring the skin parameter, and wherein on the basis of the type of skin, the analysis system is configured to select the one or more wavelengths for generating the corresponding skin sensor value.

The sensor may further comprise a sensor opening downstream of the light sources and downstream of the detector for propagation of the light source light out of the sensor and for entrance of reflected sensor light into the sensor. For instance, the system may include a wall with the sensor opening. The system may also include a distance holder or other element protruding from the system, which distance holder or other element allow arrangement of the skin to be sensed at a predefined distance from the sensor (and of the window; see below). To this end, the opening may have dimensions that prevent a substantial bulging of the skin into the sensor opening. Hence, by defining the sensor opening, the distance between skin and sensor and between skin and window can be defined.

As indicated above, the effect of applied pressure on e.g. skin gloss and/or oiliness measurements may be influenced by doming of skin. It appears that in addition or alternative to selecting specific wavelength ranges, the geometry of the sensor may also be chosen such to reduce effects on the sensor signal by changes in focal depth.

The sensor opening, may essentially have any (cross-sectional) shape. However, especially the sensor opening has one or more curved (cross-sectional) shapes, such as oval, even more is essentially circular. As indicated above, the sensor opening may not be too large. In specific embodiments, the sensor opening has an equivalent circular diameter selected from the range of 1-65 mm, such as especially 1-20 mm, like at least 3 mm. The equivalent circular diameter (or "equivalent diameter", or ECD) of an irregularly shaped two-dimensional shape is the diameter of a circle of equivalent area. For instance, the equivalent circular diameter of a square with side a is $2*a*SQRT(1/\pi)$. As indicated, the sensor opening may especially be round.

Especially good results are obtained with sensor openings that are substantially circular. Hence, in embodiments the sensor opening has a circular shape. Further, good results were obtained wherein the opening diameter (of the sensor opening) is at maximum 15 mm, such as in the range of 3-15 mm.

Further, especially the field of view of the detector and the sensor opening may be essentially the same. Therefore, the sensor may thus comprise a sensor opening downstream of the light sources and downstream of the detector for propagation of the light source light out of the sensor and for entrance of reflected sensor light into the sensor, wherein the detector has a field of view with an equivalent diameter (d5) at the sensor opening, wherein the sensor opening has an opening diameter (D2) selected from the range of $0.9 \leq d5/D2 \leq 1.1$.

Hence, the sensor may be comprised by a housing having an opening through which light may penetrate. This opening may be a full opening without a window. Optionally, the opening has a window. The window may be position receded, as to allow some skin doming (especially without touching the window).

In yet a further aspect the invention also provides a method of sensing skin gloss, the method comprises providing light source light with the system as defined herein to a skin and sensing with the system the reflected light source light reflected at the skin.

Especially, the method is a non-medical method. Especially, the method is a cosmetical method.

Also, in yet a further aspect the invention provides a data carrier having stored thereon program instructions, which when executed by the system as defined herein causes the system to execute the method as defined herein.

As indicated above, the system may comprise a polarizer. The polarizer is configured to allow only one or more specific polarizations enter the detector. Hence, in specific embodiments the sensor comprises a polarizer configured upstream of the detector. Even more especially, the polarizer comprises one or more of a segmented polarizer and a spatially varying polarizer. This allows a reduction of the influence of the (rotational) position of the detector, especially when the light sources are driven sequentially. In this way, the sensor may detect the reflected light as function of the light source. With the different polarizations of the polarizer, the sensitivity of the system may be higher.

Therefore, in specific embodiments, the device comprises a sensing mode, wherein the light sources are configured to sequentially provide the light source light. In further specific embodiments, the detector may be configured to sequentially detect reflected light source light sequentially generated by the light sources, and configured to generate corresponding detector signals. As indicated above, the system further comprises an analysis system, with the analysis system being configured to generate a corresponding skin sensor value in dependence of a sensor signal of the sensor, and in specific embodiments wherein the skin sensor value is based on an average of respective detector signals.

In embodiments, the segmented polarizer comprises a pixelated wire grid polarizer with two or more pixels having different polarization orientations. Here, the term "pixels" may also refer to areas. Especially, the sensor comprises n light sources, such as four light sources, and wherein the segmented polarizer comprises a pixelated wire grid polarizer with n pixels having polarization orientations perpendicular to each other, such as two sets of two pixels (in the case of four light sources). As indicated above, the value of n is especially at least 2, such as 3 or 4, or more.

In embodiments, the spatially varying polarizer comprises one or more of an azimuthal varying polarizer and a radial varying polarizer, which especially allows more number of emitters to be configured very close to each other.

Best results may be obtained at about the Brewster angle. Hence, in embodiments the sensor is configured to provide the light source light with optical axes (OL) under an angle of incidence ($\alpha$) with the skin at a third distance (d3), wherein the angle of incidence ($\alpha$) is selected from the range of 50-60°, even more especially wherein the angle of incidence ($\alpha$) is selected from the range of 52-56°.

Hence, amongst others herein skin gloss measurement systems and methods using sequential illumination from multiple unpolarized light emitters illuminating the skin at an angle of incidence (essentially) equal to Brewster's or polarization angle and a segmented or spatially varying polarizer in the detection path are provided.

Especially good results may (thus) be obtained when the light sources are sequentially driven. As the light sources are configured at different positions, the reflection behavior and polarization behavior, as well as an angular dependency of the reflected light may in this way provide additional information (that may result from skin structure and/or, non-uniformity of illumination) and/or may allow reducing the dependence of the sensor on the rotational position on the skin.

Hence, in specific embodiments the device comprises a sensing mode, wherein the light sources are configured to sequentially provide the light source light.

For instance, the sensors may have a measuring frequency in the range of 0.1*n-100*n Hz, wherein n is the number of light sources. With for instance 1*n Hz, each second all light sources have been consecutively illuminated the skin and the detector has (consecutively) measured possible reflections based on the respective light sources.

Of course, the use of a plurality of light sources may also allow addressing of subsets of two or more light sources. For instance, it may also be possible when four light sources are used to have two sets of two light sources, which are configured opposite of each other (with the detector in between) which sets of light sources are alternatingly switched on and off.

Also combinations of such methods may be applied, wherein e.g. in time the composition of the set of light sources may change. For instance, in a mode during a predetermined time the light sources are addressed sequentially and in a subsequent predetermined time the light sources are addressed as a group. Such mode may include a repetition of these respective predetermined times. All kind of illumination schemes may be used to further create a more reliable measuring of the skin gloss.

The detector signal may be an average over the signals generated by the respective light sources. Hence, in yet further embodiments the detector is configured to sequentially detect reflected light source light sequentially generated by the light sources, and configured to generate corresponding detector signals, wherein the system further comprises an analysis system, wherein the analysis system is configured to generate a corresponding skin sensor value in dependence of a sensor signal of the sensor, and wherein the skin sensor value is based on an average of respective detector signals. Hence, especially the detector signals are first processed and then averaged. In this way the detector signal may be an average over the signals generated by the respective light sources.

As indicated above, the system may comprise at least three light sources. Yet further, as indicated above in embodiments the sensor has a sensor optical axis (O2), and wherein the light sources are configured rotationally symmetric around the sensor optical axis (O2).

There may be a number of ways in which the sensor signal is generated. Even though many low cost devices are reported for home-use applications, the gloss measurements using these devices appear not to be quantitative and also may not correlate with the subjective perception and reference device measurements. Methods for estimating the gloss may be based on counting the number of white pixels above a certain threshold in the camera images obtained using unpolarized illumination. However, it appears that the gloss estimation based on the number of white pixels depends on the incident light intensity levels (and its fluctuations), threshold and variation in the optical properties of skin (inter and intra-individual variations), which is less desirable.

Here below, some specific embodiments are described which may provide more reliable results.

Hence, in embodiments especially the system is configured to create an image of the skin with the detector, wherein the image of the skin comprises a first area wherein maximum intensity is sensed and a second area at a first image distance from the first area, wherein the first area and second area do not overlap, wherein the system is further configured to generate the skin sensor value based on an intensity dependent of the reflected light source light along a path between the first area and the second area. The image may have an image area. The first and the second area may be areas of e.g. 0.05-30%, such as 0.05-15%, like 0.1-10% of the image area. Further, first image distance, i.e. the distance between the first area and second area, more precisely the shortest distance between the boundaries of these two areas, may be in the order of at least the area size of the first area or the second area. In general, the first area and second area may be essentially the same. Optionally, the areas may also be different but then a correction factor may be applied. Further, in general these areas are chosen square or rectangular, especially square. The area wherein a maximum intensity is sensed may be the area of the image where essentially specular reflection takes place, i.e. where the light source light is mirror like reflected and detected by the detector.

Hence, the first image distance may be in the range the square root of 0.05-30% of the image area, such as the square root of 0.05-15% of the image area, like the square root of 0.1-10% of the image area. Especially, the distance between the first area and the second area is at least 5% of the square root of the image area. Note that the image area may not have a fixed value, but may e.g. depend upon the magnification.

Further, note that the term "creating an image" and similar terms may not necessarily include the creation of a real image at a moment in time but may also refer to reading out the values of the detector at different positions over the detector surface.

It appears that information that can be derived from the two areas and/or from a (straight) line or the area in between those two areas can provide information over the glossiness, which may allow quantifying of the skin gloss (including skin oiliness), especially when the system has been calibrated (see also below).

Therefore, in embodiments the system may be configured to generate the skin sensor value based on a slope of a curve defined by the intensity of the reflected light source light along the path between the first area and the second area. Hence, based on the slope of the curve or an angle of the curve, it appears that useful skin gloss values can be generated.

Alternatively or additionally, the system may be configured to generate the skin sensor value based on an area below a curve defined by the intensity of the reflected light source light along the path between the first area and the second area. Hence, also based on the area under the curve or an angle of the curve, it appears that useful skin gloss values can be generated. The path can also be indicated as a straight trajectory or line.

Yet alternatively or additionally, the system may be configured to generate the skin sensor value based on a number of pixels of the image above a predefined threshold. Hence, based on the number of pixels above threshold also it appears that useful skin gloss values can be generated.

Further, alternatively or additionally, the system may be configured to generate the skin sensor value based on an average number of pixels of the image above predefined thresholds weighted with the corresponding pixel intensity, respectively. Therefore, also based on the weighted number of pixels above threshold useful skin gloss values can be generated.

Yet, alternatively or additionally the system may be configured to generate the skin sensor value based on a relation between an integrated intensity of the first area and the second area. Therefore, also the ratio specular to diffuse intensity of these respective ratios may be used for generating skin gloss values. For instance, when the system is calibrated with an essentially specularly reflective area and with an essentially diffuse reflective area, skin gloss parameters can be derived from the ratio specular to diffuse intensity of these respective ratios.

Further, alternatively or additionally, system is configured to define binary large objects ("blob") in the image, and wherein the system is configured generate the skin sensor value based on or more of average size and maximum size of the binary large objects in the image. Hence, based on the number of blobs and/or sizes of the blobs also useful skin gloss values can be generated. Hence, in this embodiment not the number of white pixels is used per se, but blobs are defined. Hence, also a threshold may be defined for those blobs, like at least k number of adjacent pixels over a specific intensity threshold value.

In above-mentioned embodiments, a number of times calibration has been mentioned. Especially for a quantitative evaluation of the skin gloss or skin oiliness, a calibration of the system, more precisely of the sensor (and in fact thus the detector) may be useful. This calibration can be done after production of the sensor. Alternatively or additionally, the calibration may software implemented for each sensor based on one or more earlier calibrations of example sensors. Calibration may also be part of a measuring process or may be regularly scheduled. In a specific embodiment, calibration is applied once after production of the sensor. Further, the system may include control routines that may update the calibration on the basis of sensor parameters of a reference sensor or based on e.g. drift in the signal, etc.

In specific embodiments, the system is configured to generate a corresponding skin sensor value in dependence of a sensor signal of the sensor after a flat-field correction. Flat-field correction is a technique used to improve quality in digital imaging. Flat-field correction is especially used to compensate for the artifacts from 2-D images that are caused by non-uniformity of illumination and detection, variations in the pixel-to-pixel sensitivity of the detector and/or by distortions in the optical path. As indicated above, the flat-field correction may be based on a measurement with purely diffuse reference, such as e.g. diffuse standard like Spectralon. Based on such measurements, a flat-field correction may be provided, which may be used in any measurement (as herein described).

In yet further embodiments, the system is configured to generate a corresponding skin sensor value in dependence of a sensor signal of the sensor based on an average of the respective signals of red, green, and blue channels of the detector.

BRIEF DESCRIPTION OF THE DRAWINGS

Embodiments of the invention will now be described, by way of example only, with reference to the accompanying schematic drawings in which corresponding reference symbols indicate corresponding parts, and in which.

Figure 5:
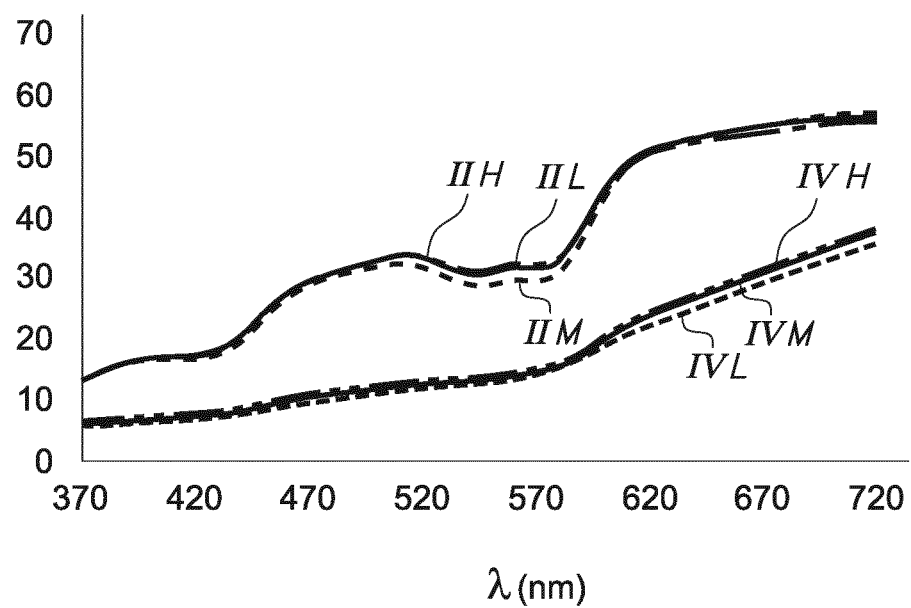
Figure 6:
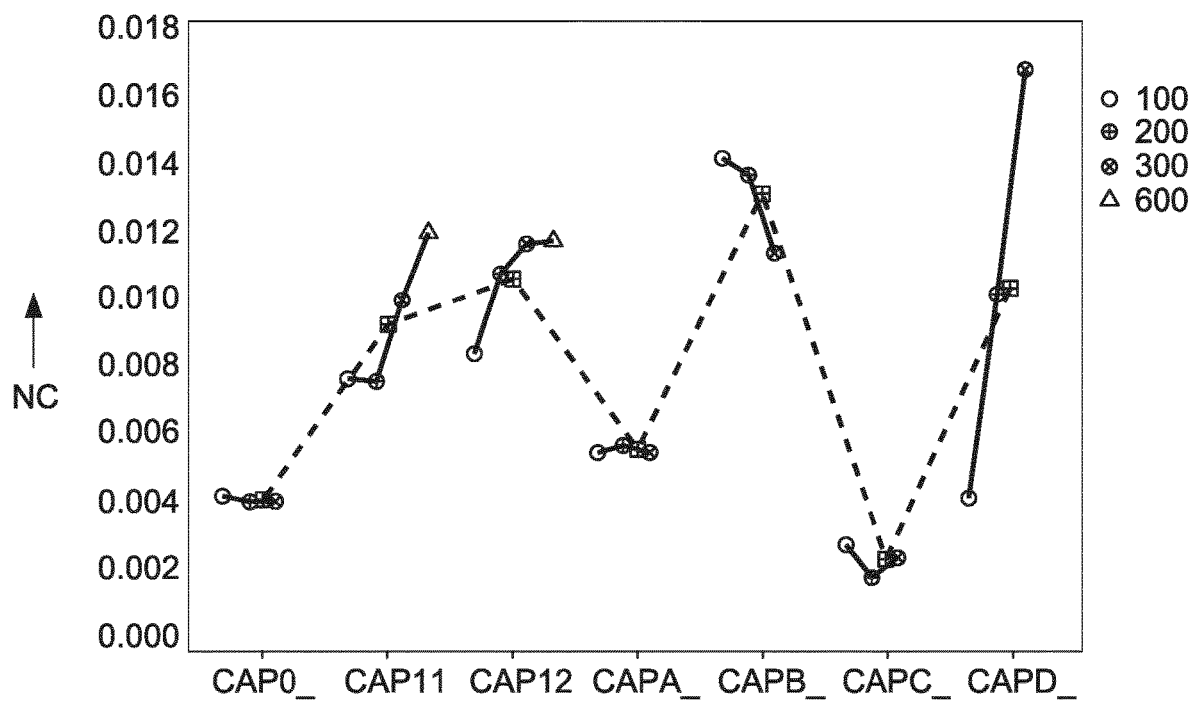
Figure 7:
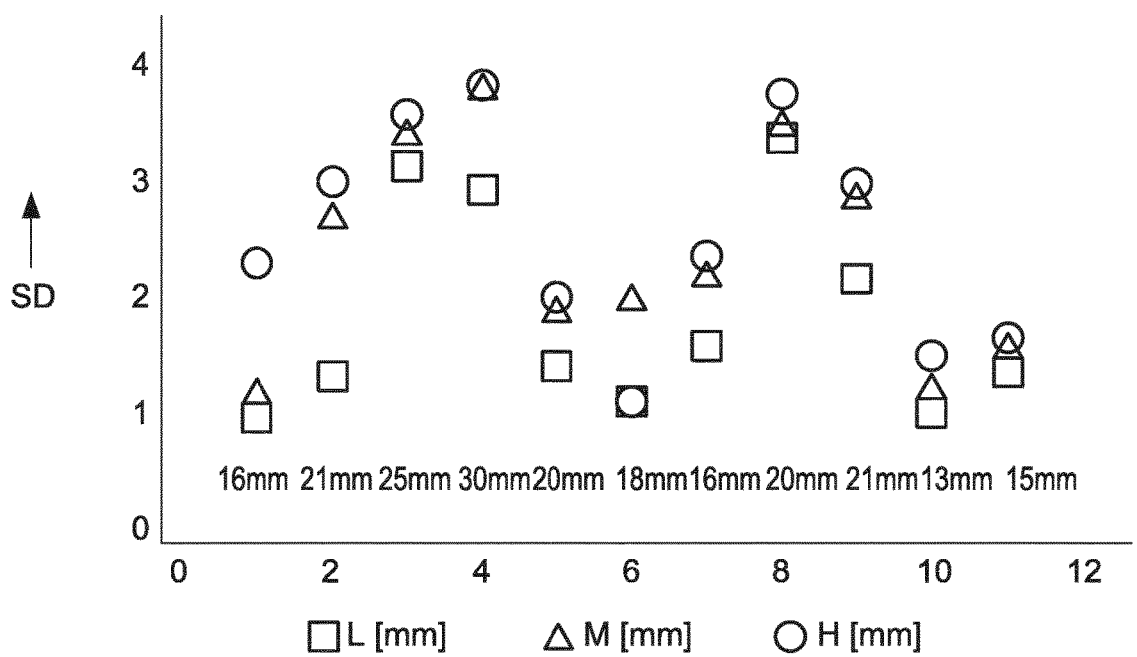

FIG. 5: shows an example of the reflectance spectra measured using a spectrometer (probe diameter of 6 mm) on skin type II and skin type VI for different applied pressure; L, M and H are again as indicated above; on the y-axis the relative spectral reflectance in arbitrary units is indicated;

FIG. 6 shows the changes in the number of pixels above a threshold measured using different caps for different applied pressure; here, the pressure is indicated in relative values 100, 200, 300, and 600; on the y-axis the number of counted of pixels is indicated. The closer the values are for different pressures, the more reliable the system is;

FIG. 7: shows skin doming measured using different caps for different pressures. Caps with internal diameter of 13 and 15 mm results in skin doming less than 2 mm and lower variation in skin doming for different applied pressures; SD refers to the skin doming (in mm); and FIG. 8: shows the maximum skin doming measured as a function of the inner diameter of the opening. The schematic drawings are not necessarily to scale.

DETAILED DESCRIPTION OF THE EMBODIMENTS

Figure 1A:
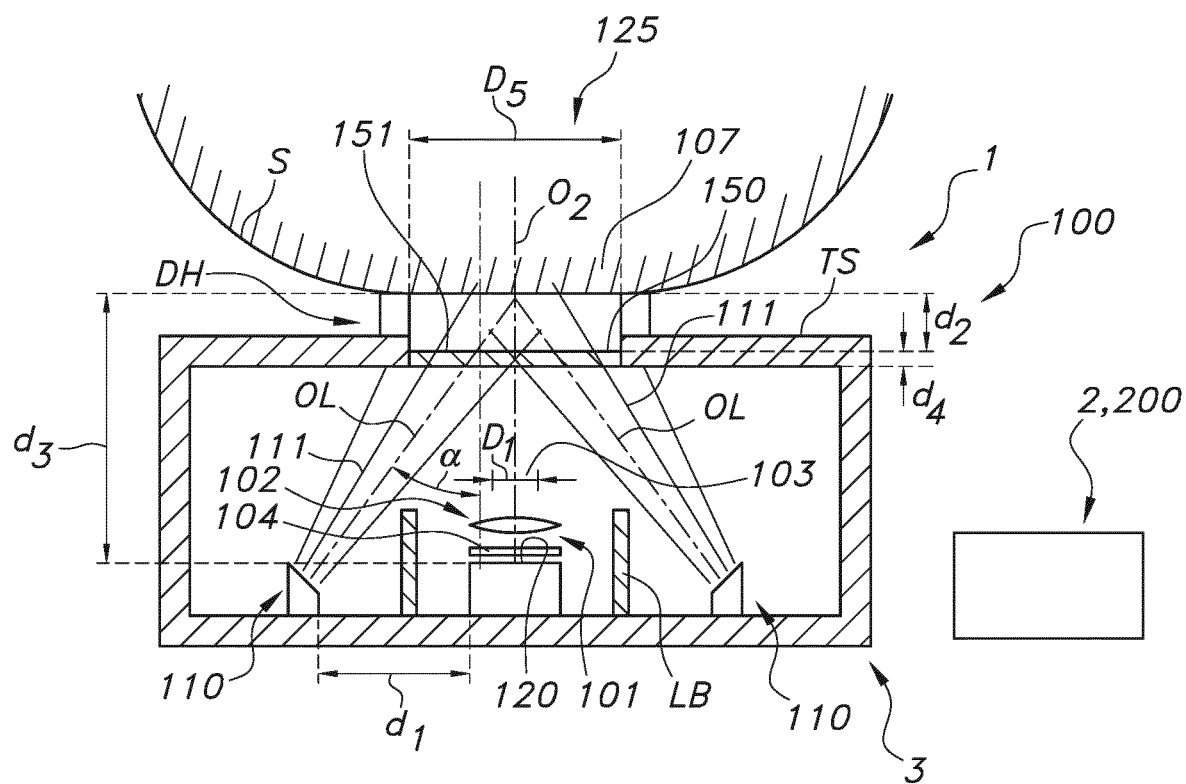
FIGS. 1a-1b schematically depict some aspects of the system.

FIG. 1*a* schematically depicts a system 1 comprising a sensor 100 for measuring a skin parameter (selected from one or more of the group consisting of skin gloss and skin oiliness). The sensor 100 comprises a plurality of spatially separated light sources 110 configured to provide light source light 111, and a detector 120 configured at a first distance d1 from each of the light sources 110. The sensor 100 is configured to provide the light source light 111 with optical axes OL under an angle of incidence a selected from the range of 10-80° with the skin at a third distance d3 and to detect reflected light source light 111. The sensor 100 may especially comprise at least three light sources 110 here, only two are depicted for the sake of understanding, wherein the light sources 110 are configured to provide unpolarized (visible) light source light 111. The first distance d1 may e.g. be selected from the range of 10-80 mm, and wherein the detector 120 is configured to detect polarized light. The dashed line S indicates the skin. Reference 150 indicates a sensor window and reference 151 indicates the sensor window material. The sensor window 150 has a sensor window thickness d4, e.g. selected from the range of 0.1-20 mm. Window 150 is optional.

The detector 120 may e.g. comprise a 2D camera 101. Further, the sensor 100 may comprise a focusing lens 102 configured downstream of the detector 120, and an aperture 103 configured downstream of the detector 120 and upstream of the focusing lens 102. The aperture 103 has a diameter D1 selected from the range of 0.1-0.8 mm. The focusing lens may e.g. be an f 5-15 mm, like 10 mm lens. Further, the system may include a second focusing lens, the combination of this lens with the first lens may provide a desired field of view and depth of focus for the overall system (see e.g. FIG. 1A). The light sources 110 are configured to provide unpolarized white light source light 111.

As indicated in FIG. 1*a*, the system 1 may further comprise an analysis system 2 wherein the analysis system 2 is configured to generate a corresponding skin sensor value in dependence of a sensor signal of the sensor 100.

The analysis system 2 may be comprised by a device that also comprise the sensor 100 (see also FIG. 1*b*), or may be comprised by a separated device. FIG. 1*a* also schematically depicts such embodiment, wherein the system 1 comprises the a skin care device 3, wherein the skin care device 3 comprises the sensor 100, and a second device 200 functionally coupled to the skin care device 3, wherein the second device 200 comprises the analysis system 2.

The sensor 100 includes an opening 107. This opening may especially be flat, i.e. its circumference may have an edge that is essentially flat. In this way, the sensor may be configured flat on the skin. The opening 107 may have a diameter D2 or equivalent diameter D2 which may be in the range of about 1-30 mm.

The opening 107 is available in a housing. The housing comprises the sensor 100.

D2 especially refers to an inner diameter, as the opening may be formed by a protruding ridge, which may have a larger (equivalent) diameter.

Reference O2 refers to the optical axis of the sensor 100. When the sensor 100 is configured on the skin, this axis may essentially coincide with a normal to the skin. As the system, more especially the sensor also has an opening 107, the optical axis may be perpendicular to a virtual plane through the opening 107, and penetrate through the center of such virtual plane. Note that the optical axis O2 here also essentially coincides with an optical axis of the detector 120.

Reference TS indicates a top surface of the sensor. This may be a planar surface. Reference LB indicates a direct light blocker, configured to prevent that light of the light sources may reach the detector without a single reflection and/or which may reduce light reaching the detector 120 that has not been reflected by the skin but by other internal surfaces of the sensor. Reference 104 refers to a polarizer.

Figure 1B:
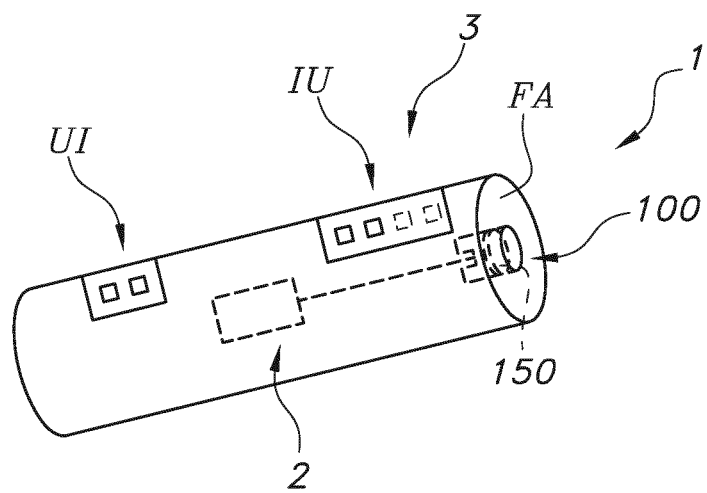

FIG. 1*b* schematically depicts an embodiment of the system 1, wherein the system 1 comprises a skin care device 3, such as skin cleansing device, skin rejuvenation device, wherein the skin care device 3 comprises the sensor 100 and the analysis system 2. The skin care device 3 may comprise an indication unit IU and/or also a user interface UI. Reference FA indicates a functional area, such as an area that may be used for massaging or exfoliating the skin.

Experiments were performed on skin type II and skin type VI for different probe pressures (low (L), medium (M), high (H)) using a spectrometer with two caps of inner diameter 6 and 12 mm respectively. Spectral reflectance measurements are obtained while varying the contact pressure of the probe of the spectrometer. It was observed that probe pressure is a variable that affects the local optical properties of the tissue and the spectral reflectance from the skin and the effect of pressure on spectral reflectance is different for different spectral bands. The amount of probe pressure applied on the skin affects the amount of blood and reflectance spectrum in a predictable manner.

Figure 3:
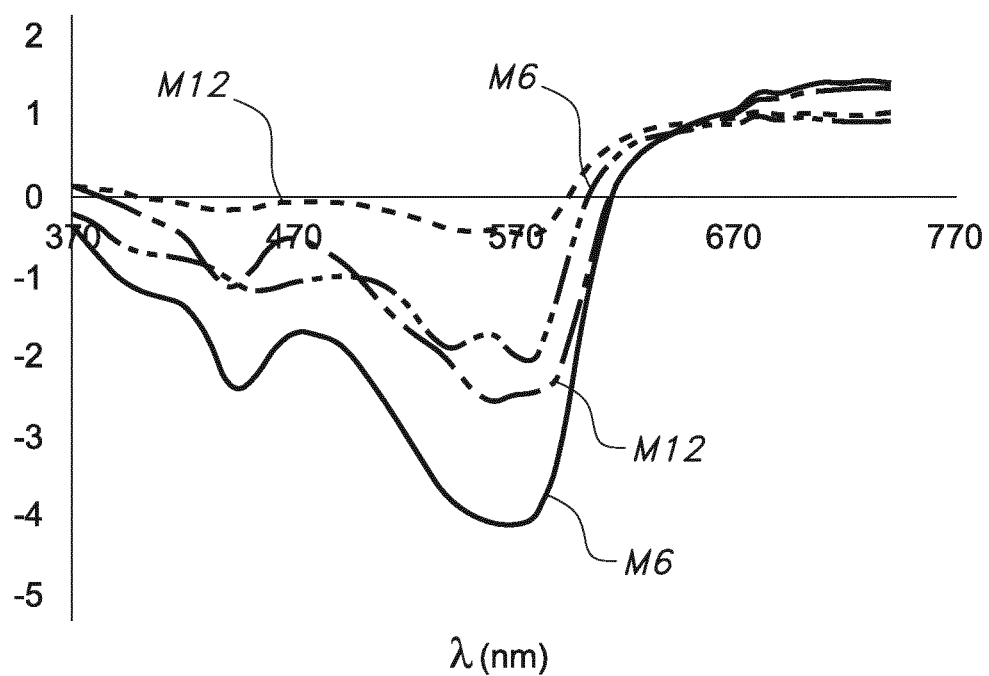
FIG. 3: shows an example of the changes in the reflectance spectra with respect to the base-line (no or low pressure) measured using a spectrometer on Caucasian skin for medium and high pressure. We have used two probes with inner diameter of 6 and 12 mm for the measurements; L, M, and H are as indicated above, the values 6 and 12 refer to the inner diameter.
Figure 4:
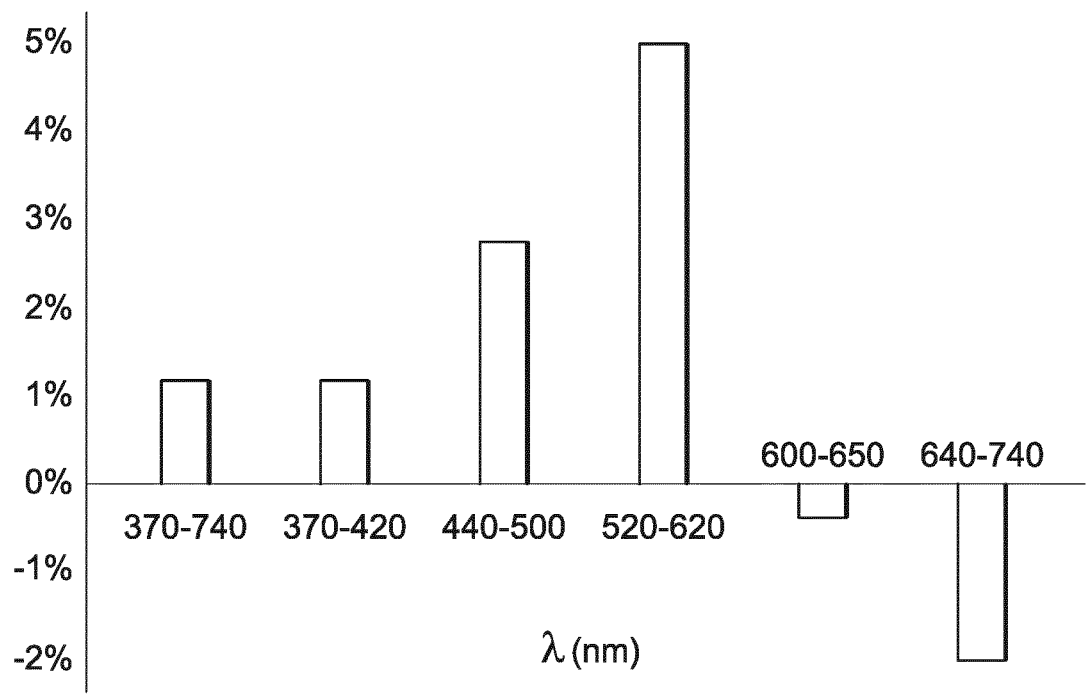
FIG. 4: shows the percentage of changes in the spectral reflectance characteristics with respect to the baseline (no or low-pressure) for different spectral bands. Spectral measurements were performed on Caucasian skin using a spectrometer with a probe diameter of 12 mm; on the y-axis, the % of change in reflectance spectra with respect to a baseline is indicated; the x-axis indicate a number of different spectral bands.

The intensity of the reflected light is decreased at wavelengths lower than 600 nm and is increased at wavelengths higher than 600 nm in comparison with the spectra corresponding to non-pressure against the skin. FIG. 3 shows the percentage of changes in the reflectance spectrum for different spectral bands. The results show that by selecting the optimal spectral bands such as 360-740 nm, 360-420 nm, 600-650 nm it would be possible to reduce the spectral variability in reflectance measurements to less than 1% and thereby the sensitivity and specificity for measuring skin characteristics such as skin oiliness and gloss can be increased.

Figure 2:
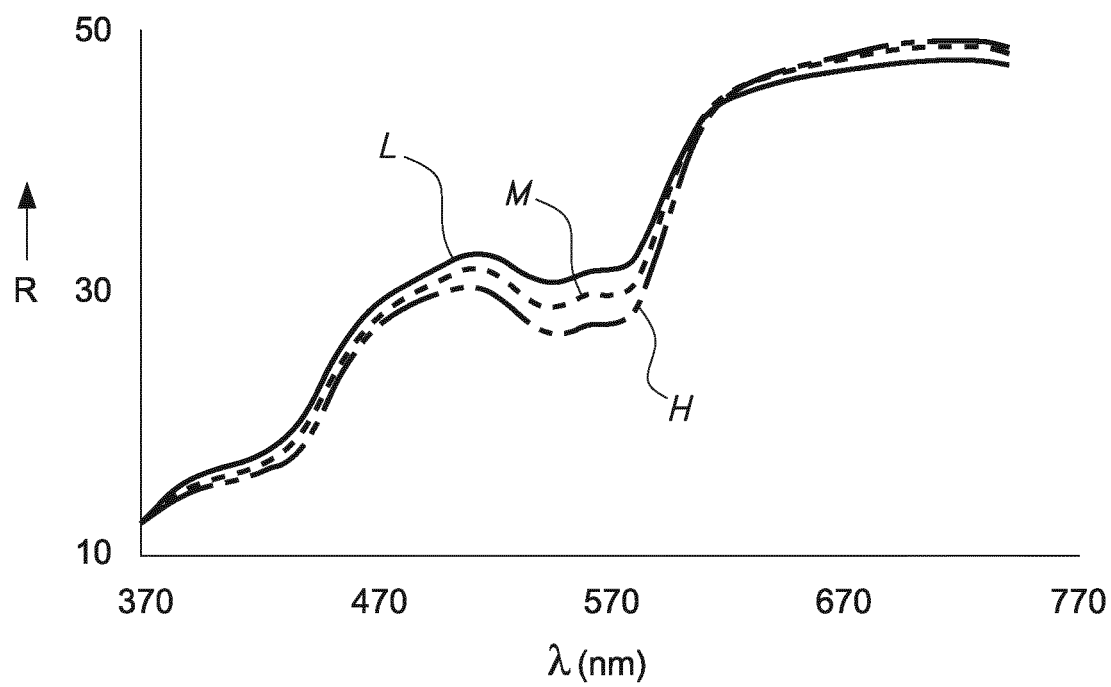
FIG. 2 shows an example of the reflectance spectra measured using spectrometer (probe diameter of 6 mm) on Caucasian skin (here skin type II) for different applied pressure; L indicates low pressure, M indicates medium pressure, and H indicates high pressure.

Deoxyhemoglobin exhibits absorption maxima at 550 nm and 760 nm, and oxyhemoglobin shows maxima at 548 nm and 576 nm. The spectra shown in FIGS. 2-3 shows the characteristic minima around 540 and 578 nm ("W" pattern)

corresponding to the absorption spectrum of oxy-hemoglobin. The "W" pattern in the diffuse reflectance spectra is more pronounced in light skin volunteers (FIGS. 3 and 5) than in dark skin ones (FIG. 5) at all the probe pressures applied. We observe that there is no remarkable difference in diffuse reflectance spectra at different pressures in the spectral band around 420 nm due to oxyhemoglobin absorption spectra.

Several types of caps were investigated, with different dimension and differently shaped openings:

| CAP type | Shape | Area ($mm^2$) | Pressure (gram) | $Gram/mm^2$ |
|---|---|---|---|---|
| A | Small round | 77 | 0, 150, 300 | 0, 2, 4 |
| B | Large round | 77 | 0, 150, 300 | 0, 2, 4 |
| C | Small rectangular | 77 | 0, 150, 300 | 0, 2, 4 |
| D | Large rectangular | 77 | 0, 150, 300 | 0, 2, 4 |
| 11 | Small rectangular but larger surface | 344 | 0, 150, 300, 600 | 0, 0.44, 0.87, 1.74 |
| 12 | Large rectangular and larger surface | 608 | 0, 150, 300, 600 | 0, 0.25, 0.49, 0.99 |

FIG. 6 shows the changes in the number of pixels above a threshold measured using different caps for different applied pressure. The larger the differences between the number of pixels as function of the pressure, the less desirable the cap is. The phrase "Small rectangular but larger surface" and similar phrases refer to the opening and the surrounding area (relatively large surface of the surrounding area and the opening is rectangular).

Figure 8:
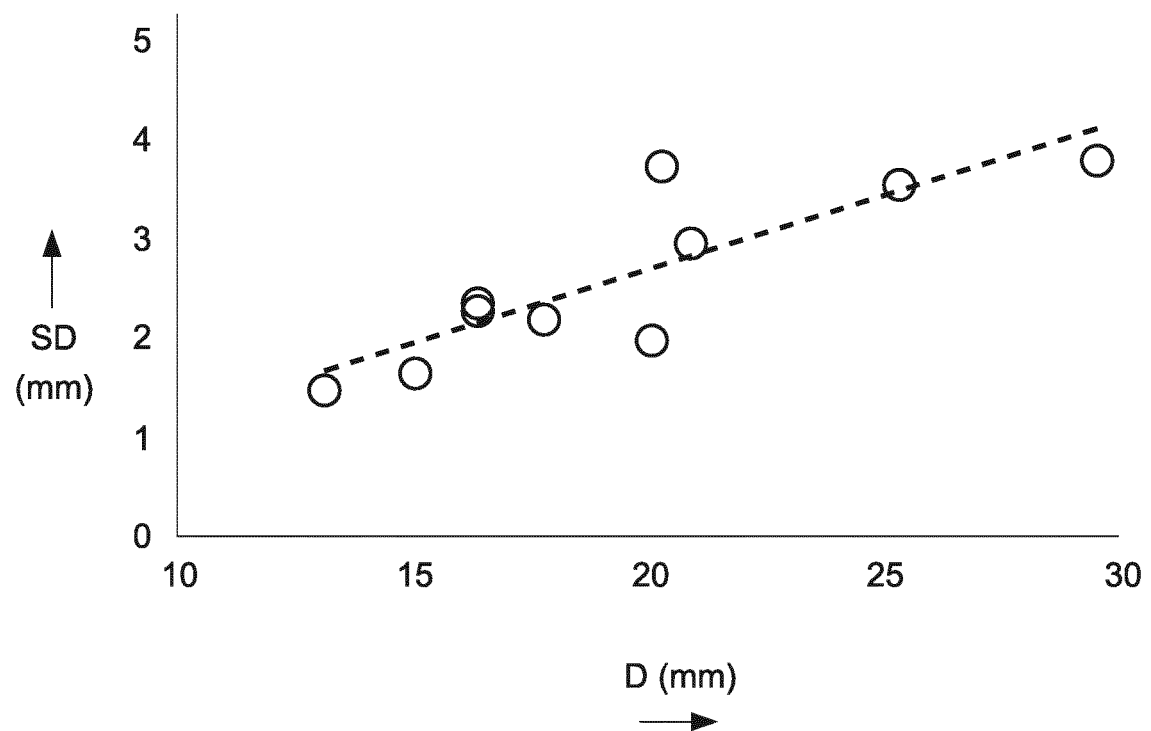

Experiments were performed for different pressure (low, medium, high) using different cap dimensions. The diameters of the cap were varied from 15 mm to 30 mm. The skin doming was measured using a sensor. Skin doming was measured was calculated as the difference in the profile measured on skin and the profile measured on a flat surface. The maximum skin doming increases with increase in internal beam diameter and was less dependent on other parameters of the contact window such as skin contact area, outer diameter. The depth of focus is desirably to be less than 2 mm. Based on the in-vivo experiments done for different pressures, we conclude that an exit window diameter of less than 15 mm results in a skin doming that is less than 2 mm (FIGS. 7-8). Possible selection criteria for the optimal cap configuration that minimize the effect of pressure is as follows: the maximum doming is less than 2 mm and the minimum variation in skin doming for low, medium and high pressure.

Hence, herein e.g. skin gloss and oiliness measurement systems and methods using circular exit window with an inner diameter less than 15 mm to minimize the dependence of skin gloss and oiliness value on the applied pressure are herein provided.

The term "substantially" herein, such as in "substantially consists", will be understood by the person skilled in the art. The term "substantially" may also include embodiments with "entirely", "completely", "all", etc. Hence, in embodiments the adjective substantially may also be removed. Where applicable, the term "substantially" may also relate to 90% or higher, such as 95% or higher, especially 99% or higher, even more especially 99.5% or higher, including 100%. The term "comprise" includes also embodiments wherein the term "comprises" means "consists of". The term "and/or" especially relates to one or more of the items mentioned before and after "and/or". For instance, a phrase "item 1 and/or item 2" and similar phrases may relate to one or more of item 1 and item 2. The term "comprising" may in an embodiment refer to "consisting of" but may in another embodiment also refer to "containing at least the defined species and optionally one or more other species".

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The devices herein are amongst others described during operation. As will be clear to the person skilled in the art, the invention is not limited to methods of operation or devices in operation.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "to comprise" and its conjugations does not exclude the presence of elements or steps other than those stated in a claim. Unless the context clearly requires otherwise, throughout the description and the claims, the words "comprise", "comprising", and the like are to be construed in an inclusive sense as opposed to an exclusive or exhaustive sense; that is to say, in the sense of "including, but not limited to". The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention further applies to a device comprising one or more of the characterizing features described in the description and/or shown in the attached drawings. The invention further pertains to a method or process comprising one or more of the characterizing features described in the description and/or shown in the attached drawings.

The various aspects discussed in this patent can be combined in order to provide additional advantages. Further, the person skilled in the art will understand that embodiments can be combined, and that also more than two embodiments can be combined. Furthermore, some of the features can form the basis for one or more divisional applications.

The invention claimed is:

1. A system comprising:
   a sensor for measuring a skin parameter of skin, the sensor comprising:
     at least three light sources configured to provide unpolarized light source light with optical axes under an angle relative to an optical axis of the sensor in a range of 10-80°, wherein the at least three light sources are spatially separated from one another, wherein the unpolarized light source light illuminates the skin;
     one or more detectors located in a central position, surrounded by the at least three light sources, at a distance from the at least three light sources, wherein the distance is in a range of 5-80 mm; and at least one lens configured to focus the unpolarized light source light reflected from the skin to the one or more detectors; and an analysis system configured to determine a type of skin for measuring the skin parameter, to select one or more wavelengths based on the determined type of skin, and to generate a corresponding skin sensor value for the skin based on a detector response of the one or more detectors at the selected one or more wavelengths.

2. The system according to claim 1, wherein the one or more wavelengths are selected in a spectral range of 370-740 nm.

3. The system according to claim 1, wherein the one or more wavelengths are selected in a spectral range of 370-420 nm, or in a spectral range of 600-650 nm.

4. The system according to claim 3, wherein the at least three light sources are configured to provide the unpolarized light source light only at one or more wavelengths in the spectral range of 370-420 nm, or at one or more wavelengths in the spectral range of 600-650 nm.

5. The system according to claim 1, wherein the one or more wavelengths are selected in a spectral range of 350-780 nm.

6. The system according to claim 5, wherein the one or more detectors comprise at least two detectors respectively configured for detection of different parts of the spectral range of 350-780 nm.

7. The system according to claim 1, wherein the sensor further comprises a sensor opening for propagation of the unpolarized light source light out of the sensor to the skin and for entrance of the reflected unpolarized light source light into the sensor.

8. The system according to claim 7, wherein each of the one or more detectors has a field of view with an equivalent diameter at the sensor opening, wherein the sensor opening has an opening diameter, wherein a ratio between the equivalent diameter at the sensor opening and the opening diameter is in a range greater than or equal to 0.9 and less than or equal to 1.1, and wherein the opening diameter is at maximum 15 mm.

9. The system according to claim 1, wherein the sensor further comprises a polarizer between the at least one lens and the one or more detectors, wherein the polarizer is configured to polarize the reflected unpolarized light source light, and wherein the one or more detectors are configured to detect the polarized reflected light.

10. The system according to claim 1, wherein the at least three light sources are configured to sequentially provide the unpolarized light source light, and wherein the one or more detectors are configured to sequentially detect the reflected unpolarized light source light, and to generate corresponding detector signals.

11. The system according to claim 1, wherein the distance is in a range of 4-20 mm, and wherein the angle is in a range of 20-60°.

12. The system according to claim 9, wherein the one or more detectors comprise a 2D camera, and wherein the sensor further comprises an aperture configured upstream of the at least one lens, wherein the aperture has a diameter in a range of 0.1-0.8 mm.

13. The system according to claim 1, wherein the analysis system is configured to generate the corresponding skin sensor value based on an average of respective detector signals provided by the one or more detectors.

14. The system according to claim 1, wherein the sensor has a sensor optical axis, and wherein the at least three light sources are configured symmetrically around the sensor optical axis.

15. The system according to claim 1, wherein the one or more detectors comprise at least two detectors having corresponding optical axes, and wherein the optical axis of the sensor is parallel to optical axes of the at least two detectors.

16. A system comprising:
a sensor for measuring a skin parameter of skin, the sensor comprising:
a plurality of light sources configured to provide unpolarized light source light for illuminating the skin with optical axes under an angle relative to an optical axis of the sensor in a range of 10-80°, wherein the plurality of light sources are spatially separated from one another; and
a detector located an equal distance from each light source of the plurality of light sources, and having an optical axis that coincides with the optical axis of the sensor, wherein the distance is in a range of 5-80 mm; and
a lens configured to focus the unpolarized light source light reflected from the skin to the detector; and
an analysis system configured to determine a type of skin for measuring the skin parameter, to select one or more wavelengths in a spectral range of 50-780 nm based on the determined type of skin, and to generate a corresponding skin sensor value for the skin based on a detector response of the detector at the selected one or more wavelengths.

17. The system according to claim 16, wherein the distance is in a range of 8-14 mm.

18. The system of claim 16, wherein the detector comprises a 2D camera, and wherein the sensor further comprises an aperture configured upstream of the lens, wherein the aperture has a diameter in a range of 0.1-0.8 mm.

19. A system comprising:
a sensor for measuring a skin parameter of skin, the sensor comprising:
at least three light sources configured to provide unpolarized light source light for illumination the skin with optical axes under an angle relative to an optical axis of the sensor in a range of 10-80°, wherein the at least three light sources are spatially separated from one another;
a detector configured at a distance from the at least three light sources, wherein the distance is in a range of 5-80 mm;
a lens configured to focus the light source light reflected from the skin to the detector; and
an analysis system configured to determine a type of skin for measuring the skin parameter, to select one or more wavelengths in a spectral range of 350-780 nm based on the determined type of skin, and to generate a skin sensor value for the skin based on a detector response of the detector at the selected one or more wavelengths.

20. The system according to claim 9, wherein the polarizer comprises one or more of a segmented polarizer and a spatially varying polarizer.

* * * * *